United States Patent [19]

Gelbfish

[11] Patent Number: 5,520,635

[45] Date of Patent: May 28, 1996

[54] METHOD AND ASSOCIATED DEVICE FOR REMOVING CLOT

[76] Inventor: Gary A. Gelbfish, 2502 Ave. I, Brooklyn, N.Y. 11210

[21] Appl. No.: 358,209

[22] Filed: Dec. 16, 1994

[51] Int. Cl.$^6$ .................................................... A61B 17/20
[52] U.S. Cl. .............................. 604/22; 604/53; 606/159; 606/169; 606/170
[58] Field of Search ...................... 604/22, 53; 606/159, 606/169, 170, 128, 46

[56] References Cited

U.S. PATENT DOCUMENTS

| | | |
|---|---|---|
| 4,986,807 | 1/1991 | Farr . |
| 4,994,067 | 2/1991 | Summers . |
| 5,419,774 | 5/1995 | Willard et al. . |
| 5,429,136 | 7/1995 | Milo et al. . |
| 5,431,673 | 7/1995 | Summers et al. . |

*Primary Examiner*—C. Fred Rosenbaum
*Assistant Examiner*—Perry E. Van Over
*Attorney, Agent, or Firm*—R. Neil Sudol; Henry D. Coleman

[57] ABSTRACT

A method for removing a clot utilizes a surgical instrument or device including an elongate tubular member having a most distal first opening, a relatively central second opening and a most proximal third opening all spaced from each other along the tubular member. The distal end of the tubular member is inserted through a skin surface of a patient into a subcutaneous blood vessel or vascular bypass and subsequently out of the vascular component and the skin surface so that the first opening and the third opening are located outside the patient while the second opening is located in the vascular component. Upon completed insertion of the device, suction is applied to one of the openings outside the patient to thereby draw a blood clot in the blood vessel or vascular bypass towards the second opening which is disposed in the vessel, graft or bypass. Upon a drawing of the clot at least partially into the tubular member through the second opening, a portion of the clot is severed inside the tubular member and is subsequently removed from the tubular member through the suction opening in the tubular member.

17 Claims, 1 Drawing Sheet

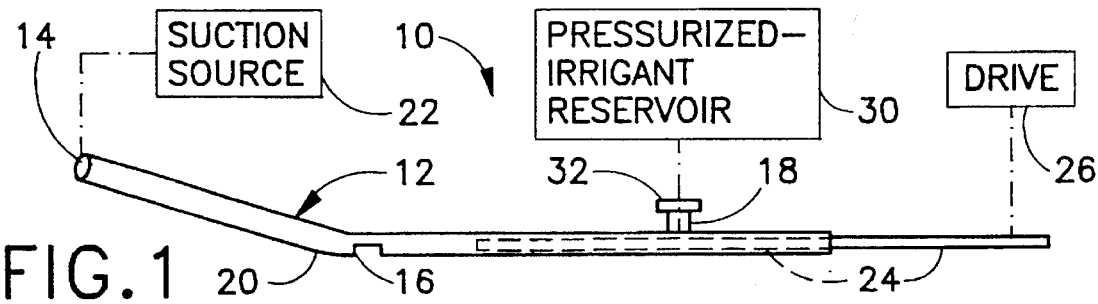
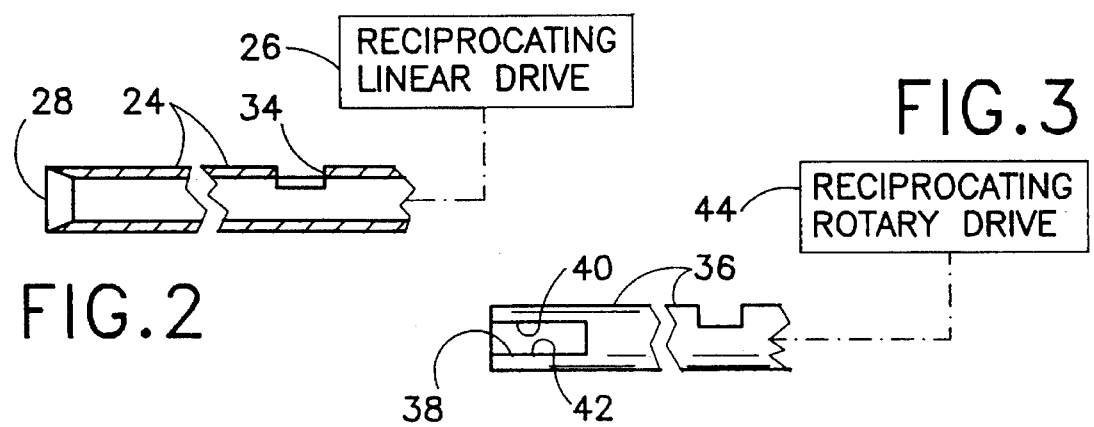
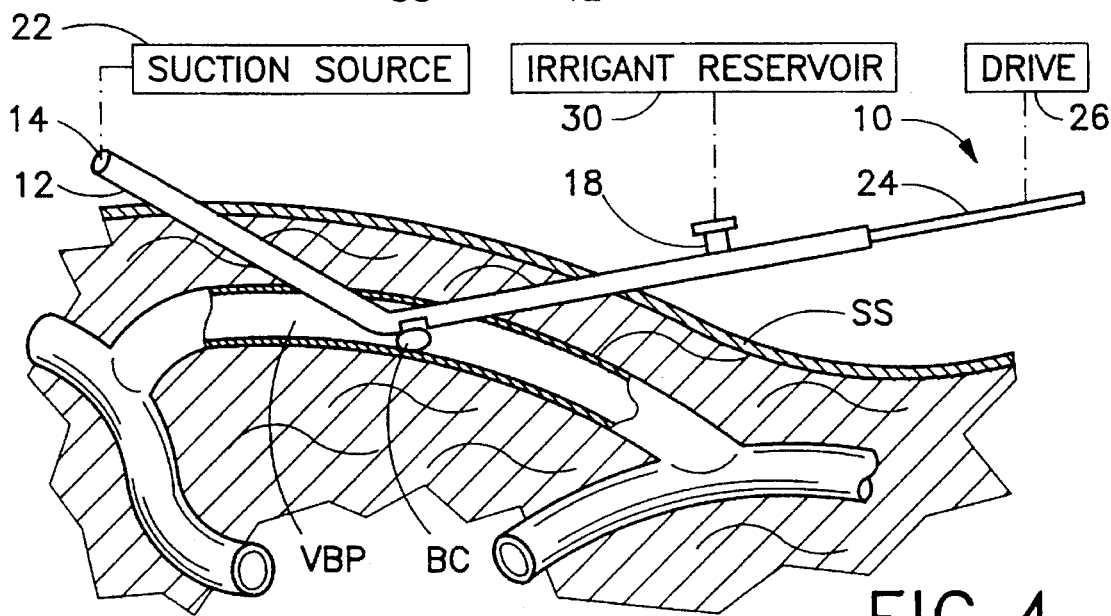
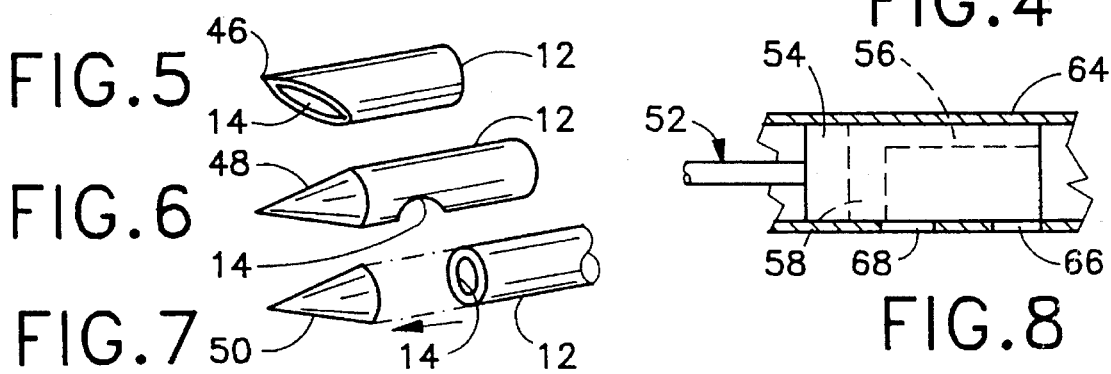

5,520,635

METHOD AND ASSOCIATED DEVICE FOR REMOVING CLOT

BACKGROUND OF THE INVENTION

This invention relates to a method and an associated device for removing a vascular clot. The method and device are especially useful for removing clots from subcutaneous vascular bypasses or shunts.

Vascular bypasses, whether made of human (graft) tissue or polymeric material, become regularly blocked with blood clots which must be removed. A common technique for cleaning clogged vascular bypasses is surgical: the skin surface and the underlying shunt are cut open and instruments are inserted through the openings to extract clumps of clotted blood.

The disadvantages of this conventional surgical procedure are well known. Because of the blood which naturally spurts out through the incision, the cleaning of the graft or bypass must be performed in the operating room. Of course, all the disadvantages or side-effects of surgery pertain: pain to the patient, danger of infection, loss of blood, as well as time and expense due to the requisite hospital staff.

Another common method of cleaning clogged vascular bypasses is dissolution of the clot via biological enzymes. The most common enzyme in current use is urokinase. The disadvantages of this method include high cost of the enzymes and a delay of as much as several hours while the enzyme acts on the clot. Systemic side effects of these enzymes, notably bleeding at other sites in the body due to unwanted yet uncontrolled dissolution of other "good" clots, are also seen.

OBJECTS OF THE INVENTION

An object of the present invention is to provide a new technique for removing a vascular clot, such as a clot in a subcutaneous vascular bypass.

Another object of the present invention is to provide an associated instrument or device for performing the technique.

A further object of the present invention is to provide such a technique which reduces, if not eliminates, at least one or more disadvantages of conventional surgical or enzymatic clot removal techniques.

Another, more particular, object of the present invention is to enable the removal of high viscosity clots using tubes of small diameter.

Yet another particular object of the present invention is to provide such a technique or method which reduces the time required to remove a subcutaneous vascular clot.

These and other objects of the present invention will be apparent from the drawings and detailed descriptions herein.

SUMMARY OF THE INVENTION

A method for removing a clot in accordance with the present invention utilizes a surgical instrument or device including an elongate tubular member having a most distal first opening, a relatively central second opening and a most proximal third opening all spaced from each other along the tubular member. The method includes the step of inserting a distal end of the tubular member through a skin surface of a patient into a subcutaneous tubular vascular component (a blood vessel or bypass) and subsequently out of the vascular component and the skin surface so that the first opening and the third opening are located outside the patient while the second opening is located in the vascular component. Upon completed insertion of the device, suction is applied to one of the first opening and the third opening to thereby draw a blood clot in the vascular component towards the second opening which is disposed in the vessel, graft or bypass. Upon a drawing of the clot at least partially into the tubular member through the second opening, a portion of the clot is severed inside the tubular member and is subsequently removed from the tubular member through the first opening or the third opening, whichever is connected to the suction source.

According to another feature of the present invention, the severing of the clot portion includes the steps of providing an obturator element inside the tubular member and shifting the obturator element longitudinally along the tubular member. Where the obturator element is at least partially hollow, the method further comprises the step of feeding an irrigation fluid at least partially along the obturator element from that opening in the tubular member which is outside the patient and is not connected to a suction source.

Where the obturator element includes a cutting edge at one end and an aperture spaced from the cutting edge, the step of severing includes the step of cutting the clot with the cutting edge of the obturator element. The method then further comprises the step of aligning the aperture in the obturator element with the irrigation opening to permit feeding of the irrigation fluid during the step of feeding.

According to another feature of the present invention, the shifting of the obturator element includes the step of reciprocating the obturator element inside the tubular member in the manner of a piston inside a cylinder.

According to another feature of the present invention, removal of the severed clot portion from the tubular member is implemented at least in part by pushing the severed portion of the clot towards the suction opening in the tubular member.

The pushing of the severed clot portion may be accomplished in part by shifting the obturator element longitudinally along the tubular member. Alternatively or additionally, the pushing of the severed clot portion is accomplished by the irrigation fluid. In a preferred embodiment of the invention, the irrigation fluid is pressurized and flows into the tubular member only upon the severing of the clot portion. The aperture in the obturator element aligns with the irrigation opening and acts therewith as an opened valve for enabling the flow of the pressurized irrigant.

According to an additional feature of the present invention, the removal of the clot pieces may be assisted by using suction to pull the severed portion of the clot towards the suction opening in the tubular member. It is to be noted that in some cases, suction and a reciprocating and/or rotary cutter or obturator may be sufficient to expel clot debris.

The severing or cutting of the clot may include rotating an obturator element inside the tubular member, the obturator element having a cutting edge juxtaposable to the middle opening.

A device for removing a clot comprises, in accordance with the present invention, an elongate tubular member having a most distal first opening, an intermediately located second opening and a most proximal third opening all spaced from each other along the tubular member. A vacuum generator is operatively connected to the first opening for applying suction to the tubular member. A cutting element is disposed at least partially in the tubular member and has a cutting blade juxtaposable to the second opening for severing a clot drawn partially in through the second opening upon disposition of the tubular member through a skin surface so that the first opening and the third opening are located outside the patient while the second opening is located in a subcutaneous vascular component. An irrigation reservoir or supply is operatively connected to the third opening for feeding an irrigation fluid to the tubular member upon a severing of a portion of the clot by the cutting element.

Pursuant to another feature of the present invention, the cutting element takes the form of a tubular obturator slidably disposed inside the tubular member. In this case, the blade may be disposed on a distal edge of the obturator.

Pursuant to a further feature of the present invention, the tubular member is provided with a bend to facilitate insertion of the tubular member into the subcutaneous vascular component during a clot removal operation.

Pursuant to an additional feature of the present invention, the second or intermediate opening is spaced by a predetermined distance from the third opening, while the cutting element includes a tubular obturator having a cutting edge and an aperture spaced by the same predetermined distance from the cutting edge, so that the aperture is juxtaposed to the third opening upon juxtaposition of the cutting edge to the second opening during a shifting of the obturator along the tubular member.

Pursuant to another feature of the present invention, an automatic drive is operatively connected to the cutting element for reciprocating the cutting blade inside the tubular member and past the second opening.

The present invention thus provides a technique and an associated device for removing a vascular clot, such as a clot in a subcutaneous vascular bypass. The technique reduces, if not eliminates, one or more disadvantages of conventional surgical clot removal techniques. For example, the technique reduces the time required to remove surgically a subcutaneous vascular clot. Reduced time means less blood loss and reduced surgical costs. The technique also requires less time than enzymatic treatment and eliminates the expense of costly enzymes.

BRIEF DESCRIPTION OF THE DRAWING

FIG. 1 is partially a schematic side elevational view and partially a block diagram of a device for removing a subcutaneous blood clot, in accordance with the present invention.

FIG. 2 is partially a schematic longitudinal cross-sectional view and partially a block diagram showing a cutting component of the device of FIG. 1.

FIG. 3 is partially a schematic side elevational view and partially a block diagram showing an alternative cutting component for the device of FIG. 1.

FIG. 4 is partially a schematic cross-sectional view of subcutaneous tissues and a vascular bypass and partially a schematic side elevational view of the device of FIG. 1, showing a step in an operation removing a clot in the bypass.

FIGS. 5–7 are schematic partial perspective views of respective alternative embodiments of the distal end of tubular member 12, on an enlarged scale.

FIG. 8 is a schematic partial cross-sectional view of a modified obturator in accordance with the present invention.

DETAILED DESCRIPTION

As illustrated in FIG. 1, a surgical instrument or device 10 for removing a blood clot from a patient comprises an elongate tubular member 12 having a most distal first opening 14, an intermediately located second opening 16 and a most proximal third opening 18 all spaced from each other along the tubular member. Tubular member 12 is provided with a bend or elbow 20 for facilitating the insertion of the distal end portion of the instrument into a patient so that distal opening 14 and proximal opening 18 both lie outside the patient, while intermediate opening 16 lies inside a subcutaneous blood vessel, graft or vascular bypass VBP (FIG. 4).

A vacuum generator or suction source 22 is operatively connected to distal opening 14 for applying suction to tubular member 12. A hollow obturator 24 is shiftably inserted inside tubular member 12. At a proximal end, obturator 24 is operatively connected to an automatic reciprocating linear or translatory drive 26, while at a distal end the obturator 24 is provided with a circular blade or cutting edge 28 (FIG. 2). Drive 26 reciprocates obturator 24 back and forth across intermediate opening 16. Upon a retraction stroke, intermediate opening 16 is uncovered by obturator 24 to permit suction from suction source 22 to draw a blood clot BC in bypass VBP partially into the tubular member 12 through intermediate opening 16 (see FIG. 4). A subsequent distally directed stroke of obturator 24 pushes cutting edge 28 against blood clot BC, thereby severing or macerating a portion thereof.

As further illustrated in FIG. 1, a supply or reservoir 30 is operatively connected via a luer lock or similar function adapter 32 to proximal opening 18 for feeding a saline irrigation fluid to tubular member 12 upon a severing of a portion of blood clot BC by cutting edge 28 of obturator 24. The forward pushing motion of obturator 24 serves in part to assist the pulling action of suction source 22 to remove the severed clot portion from tubular member 12. A greater push is provided, however, by the saline irrigant from supply or reservoir 30. The irrigant is placed under pressure to facilitate the removal of severed clot portions from tubular member 12.

Obturator 24 is provided with an aperture 34 spaced from cutting edge 28 by approximately the same distance as that between intermediate opening 16 and proximal opening 18. Thus, upon a severing of blood clot BC during a distally directed stroke of obturator 24, obturator 24 is connected to pressurized irrigant reservoir 30 via proximal opening 18 and aperture 34, thereby providing a timely flow of irrigant to force the severed clot material from tubular member 12. This pushing action is believed to so facilitate the removal of severed clot material that obturator 24 and tubular member 12 can be constructed with diameters thinner than those which might have only suction forces to remove severed clot material. Accordingly, small diameter tubes may be used to remove clots of relatively high density.

Aperture 34 and proximal opening 18 cofunction as a valve to permit the flow of irrigant only upon a severing of a blood clot BC by cutting edge 28 of obturator 24. During the pressurization of obturator 24 by the irrigant from reservoir 30, obturator 24 is juxtaposed to intermediate opening 16 so as to prevent the flow of pressurizing fluid into bypass VBP. This juxtaposition occurs periodically inasmuch as the invention contemplates an alternating cycle: initially a vacuum and other assist devices suck clots into the tubular clot-removal device. Only after that has been accomplished and the obturator changes position does the pressure cycle commence during which the obturator and/or pressurized saline solution ejects the clot material.

As shown in FIG. 2, cutting edge 28 is a circular edge provided by beveling obturator 24 at a distal end thereof.

As shown in FIG. 3, an obturator element 36 insertable inside tubular member 12 is provided at a distal end with a longitudinally extending slot 38 formed along longitudinal edges with blades 40 and 42 for alternately slicing off portions of a blood clot sucked into tubular member 12 through intermediate opening 16 by operation of suction source 22. Obturator element 36 is operatively connected at a proximal end to a reciprocating rotary drive 44. Drive 44 functions to shift blades 40 and 42 alternately past intermediate opening 16.

It is to be noted that rotary drive 44 may be sufficient to macerate a clot to a particle size suitable for evacuation through tubular member 12 by suction. However, obturator element 36 may be additionally connected to a reciprocating drive for facilitating clot particle ejection or removal. Pressurized saline may or may not be provided. The requirements will vary depending on the characteristics of the particular clots.

As depicted in FIG. 4, a distal end of tubular member 12 is inserted through a skin surface SS of a patient into a subcutaneous tubular vascular component in the form of bypass VBP and subsequently out of bypass VBP and skin surface SS so that distal opening 14 and proximal opening 18 are located outside the patient while intermediate opening 16 is located in bypass VBP. Upon completed insertion of the device, suction source 22 is operated to apply suction to distal opening 14 to thereby draw blood clot BC in bypass VBP towards intermediate opening 16. Upon a drawing of the clot at least partially into tubular member 12 through intermediate opening 16, a portion of the clot is severed inside tubular member 12 by a distally directed stroke of obturator 24 or an angular shifting of obturator element 36. Subsequently, the severed clot portion is removed from tubular member 12 through distal opening 14, in part because of the feeding of irrigant under pressure from reservoir 30 and in part because of the suction applied by source 22.

It is to be noted that the present invention is used in conjunction with conventional mechanical surgical techniques for drawing clot material from opposite ends of bypass VBP towards intermediate opening 16. For example, a wire (not illustrated) inserted through the same or a different puncture site may be manipulated to catch clotted clumps of blood and drag the captured clumps towards intermediate opening 16 where the clumps are subjected to a suction force tending to draw the clot material into intermediate opening 16. Also, Fogarty balloon catheters (not illustrated) may be used to push the clots, or another catheter (not illustrated) may inject fluid under pressure into the bypass graft to enhance further the flow of the clot to intermediate opening 16 and out through tubular member 12.

FIGS. 5–7 illustrate respective alternative embodiments of the distal end of tubular member 12. As shown in FIG. 5, a sharp point 46 for skin penetration is provided by beveling the entire distal end of tubular member 12. Alternatively, as depicted in FIG. 6, the distal most opening 14 in tubular member 14 is spaced from a sharpened distal tip 48 of the tubular member. As illustrated in FIG. 7, a tapered or sharpened distal tip 50 of tubular member 12 may be severed or otherwise separated from the rest of the tubular member, thereby forming opening 14.

As shown in FIG. 8, an obturator 52 extending through a vascular access tube 64 as described hereinabove may have a substantially solid distal end portion 54. That end portion 54 is formed with a groove 56 and a passageway 58 for enabling the transmission of irrigant from a proximal most opening 68 in a distal direction upon the completion of a cutting stroke of obturator 52 at an intermediate opening 66. Alternatively, a solid, but loosely fitting, obturator may be used, where pressurized irrigant flows around the obturator.

Although the invention has been described in terms of particular embodiments and applications, one of ordinary skill in the art, in light of this teaching, can generate additional embodiments and modifications without departing from the spirit of or exceeding the scope of the claimed invention. For example, other configurations of openings 14, 16 and 18 and other clot cutting techniques will occur readily to those of ordinary skill in the art. These alternate configurations and cutting tools are considered to be equivalent to those disclosed specifically herein.

Accordingly, it is to be understood that the drawings and descriptions herein are proffered by way of example to facilitate comprehension of the invention and should not be construed to limit the scope thereof.

What is claimed is:

1. A method for removing a clot, comprising the steps of:

providing an elongate tubular member having a most distal first opening, a relatively central second opening and a most proximal third opening all spaced from each other along said tubular member;

inserting a distal end of said tubular member through a skin surface of a patient into a subcutaneous tubular vascular component underlying said skin surface and subsequently out of said vascular component and said skin surface so that said first opening and said third opening are located outside the patient while said second opening is located in said vascular component;

upon completion of said step of inserting, applying suction to one of said first opening and said third opening to thereby draw a blood clot in said vascular component towards said second opening;

upon a drawing of said clot at least partially into said tubular member through said second opening, severing a portion of said clot inside said tubular member; and removing the severed portion of said clot from said tubular member through said one of said first opening and said third opening.

2. The method defined in claim 1 wherein said step of severing includes the steps of providing an obturator element inside said tubular member and shifting said obturator element longitudinally along said tubular member.

3. The method defined in claim 2 wherein said obturator element is at least partially hollow, further comprising the step of feeding an irrigation fluid at least partially along said obturator element from the other of said first opening and said third opening.

4. The method defined in claim 3 wherein said obturator element includes a cutting edge at one end and an aperture spaced from said cutting edge, said step of severing including the step of cutting said clot with said cutting edge, further comprising the step of aligning said aperture with said other of said first opening and said third opening to permit feeding of said irrigation fluid during said step of feeding.

5. The method defined in claim 2 wherein said step of shifting includes the step of reciprocating said obturator element inside said tubular member in the manner of a piston inside a cylinder.

6. The method defined in claim 1 wherein said step of removing includes the step of pushing said severed portion of said clot towards said one of said first opening and said third opening.

7. The method defined in claim 6 wherein said step of pushing includes the steps of providing an obturator element inside said tubular member and shifting said obturator element longitudinally along said tubular member.

8. The method defined in claim 6 wherein said step of pushing includes the steps of connecting a pressurizable fluid source to said tubular member at the other of said first opening and said third opening and feeding fluid under pressure from said source and at least partially along said tubular member towards said one of said first opening and said third opening.

9. The method defined in claim 1 wherein said step of removing includes the step of using suction to pull said severed portion of said clot towards said one of said first opening and said second opening.

10. The method defined in claim 1 wherein said step of providing includes the step of providing said tubular member with a bend to facilitate said step of inserting.

11. The method defined in claim 1 wherein said step of severing includes the steps of providing an obturator element inside said tubular member and rotating said obturator element inside said tubular member, said obturator element having a cutting edge juxtaposable to said second opening.

12. A device for removing a clot, comprising:

an elongate tubular member having a most distal first opening, an intermediately located second opening and a most proximal third opening all spaced from each other along said tubular member;

vacuum generator means operatively connected to said first opening for applying suction to said tubular member;

cutting means disposed at least partially in said tubular member and having a cutting blade juxtaposable to said second opening for severing a clot drawn partially in through said second opening upon disposition of said tubular member through a skin surface so that said first opening and said third opening are located outside the patient while said second opening is located in a subcutaneous vascular component; and irrigation means operatively connected to said third opening for feeding an irrigation fluid to said tubular member upon a severing of a portion of said clot by said cutting means.

13. The device defined in claim 12 wherein said cutting means includes a tubular obturator slidably disposed inside said tubular member.

14. The device defined in claim 13 wherein said cutting blade is disposed on a distal edge of said obturator.

15. The device defined in claim 12 wherein said tubular member is provided with a bend to facilitate insertion of said tubular member into said subcutaneous vascular component during a clot removal operation.

16. The device defined in claim 12 wherein said second opening is spaced by a first predetermined distance from said third opening, said cutting means including a tubular obturator having said cutting blade and an aperture spaced by a second predetermined distance from said cutting blade, said second predetermined distance being approximately equal to said first predetermined distance so that said aperture is juxtaposed to said third opening upon juxtaposition of said cutting blade to said second opening during a shifting of said obturator along said tubular member.

17. The device defined in claim 12, further comprising automatic shifting means operatively connected to said cutting means for reciprocating said cutting blade inside said tubular member and past said second opening.

* * * * *